United States Patent

Grundmann et al.

[11] Patent Number: 5,188,933
[45] Date of Patent: Feb. 23, 1993

[54] PROTEIN PP15 PREPARED BY GENETIC MANIPULATION

[75] Inventors: Ulrich Grundmann, Lahntal-Grossfelden; Karl-Josef Abel; Eugen Amann, both of Marburg, all of Fed. Rep. of Germany

[73] Assignee: Behringwerke Aktiengesellschaft, Marburg/Lahn, Fed. Rep. of Germany

[21] Appl. No.: 709,790

[22] Filed: Jun. 3, 1991

Related U.S. Application Data

[63] Continuation of Ser. No. 324,068, Mar. 16, 1989, abandoned.

[30] Foreign Application Priority Data

Mar. 18, 1988 [DE] Fed. Rep. of Germany ....... 3809119

[51] Int. Cl.$^5$ .................. C07H 15/12; C12Q 1/68; C12N 15/00; C12N 1/00
[52] U.S. Cl. .................. 435/6; 435/320.1; 435/172.2; 435/252.3; 435/69.1; 435/172.3; 536/23.5
[58] Field of Search ............. 435/6, 172.3, 320, 252.3, 435/252.33, 255, 69.1; 536/27

[56] References Cited

U.S. PATENT DOCUMENTS 4,348,316 9/1982 Bohn ................. 260/112 R

OTHER PUBLICATIONS

Neufeld et al, *Biochemistry of Glycoproteins & Proteoglycans* 1980 Plenum Press, N.Y., pp. 241-266.
Westerwoudt, Methods in Enzymology 121, pp. 3-18 (1986) Academic Press Inc., N.Y., N.Y.
Lane et al., Ibid pp. 183-192.
Grundmann et al, Nuc Acids Res 16(10) p. 4721 (1988).
Grundmann et al, Proc Natl Acad Sci 83 8024-8028 (1986).
Haschemeyer et al, Proteins: Guide to Study by Physical and Chemical Methods (1973) John Wiley & Sons N.Y., N.Y., pp. 78-93.
Nikaido et al, Nature 311, pp. 631-636 (1984).
R. Lathe, J. Mol. Biol., 183 (1985) pp. 1-12.
Chirgwin et al., Biochemistry, 18 (1979) pp. 5294-5299.
Aviv et al. Proc. Natl. Acad. Sci. USA, 69, No. 6 (1979) pp. 1408-1412.
Gubler et al., Gene 25 (1983) pp. 263-269.
T. Maniatis et al., Molecular Cloning, A Laboratory Manual, Cold Spring Harbour (1982), pp. 242-246.
Enquist et al., Methods in Enzymology, 68 (1979) pp. 281-298.

*Primary Examiner*—Margaret Moskowitz
*Assistant Examiner*—Scott A. Chambers
*Attorney, Agent, or Firm*—Finnegan, Henderson, Farabow, Garrett and Dunner

[57] ABSTRACT

The cDNA coding for PP15 is described. This cDNA can be used to prepare PP15 in pro- or eukaryotic cells.

12 Claims, 3 Drawing Sheets

```
         10                    30                         50
GGAAGGGACAGTCGGCCGCCAGACCGGCTGGGTTGCCCTGCCGCTGCCCTGCCATCGTGCC
                 70                     90                  110
AGCCCCTCGGGTCTCCGTGAGGCCGGGTGACGCTCCAGAATGGAGACAAGCCAATTTGG
                                             M  G  D  K  P  I  W 130                   150                     170
GAGCAGATTGGATCCAGCTTCATTCAACATTACTACCAGTTATTGATAATGATAGAACC
 E  Q  I  G  S  S  F  I  Q  H  Y  Y  Q  L  F  D  N  D  R  T 190                  210                    230
CAACTAGGCGCAATTTACATTGACGCGTCATGCCTTACGTGGGAAGGACAACAGTTCCAG
 Q  L  G  A  I  Y  I  D  A  S  C  L  T  W  E  G  Q  Q  F  Q 250                  270                    290
GGGAAAGCTGCCATTGTGGAGAAGTTGTCTAGCCTTCCGTTCCAGAAAATTCAGCACAGC
 G  K  A  I  V  E  K  L  S  S  L  P  F  Q  K  I  Q  H  S 310                  330                    350
ATCACCGGCCAGGACCATCAGCCCACTCCAGATAGCTGCATCATCAGCATGGTTGTGGGC
 I  T  A  Q  D  H  Q  P  T  P  D  S  C  I  I  S  M  V  V  G

FIG.2
```

```
                370                          390                           410
CAGCTTAAGGCGGATGAAGACCCCATCATGGGGTTCCACCAGATGTTCCTATTAAAGAAC
 Q   L   K   A   D   E   D   P   I   M   G   F   H   Q   M   F   L   L   K   N
                430                          450                           470
ATCAACGATGCTTGGGTTTGCACCAATGACATGTTCAGGCTCGCCCTGCACAACTTTGGC
 I   N   D   A   W   V   C   T   N   D   M   F   R   L   A   L   H   N   F   G
                490                          510                           530
TGACCTCCTCTCAGCTAGGCACTCACGCTGTTTCCTCCCTCCTCCTTCCAATACTAT
                550                          570                           590
TCCCACTCCTCCAGATGCTCCAAATATCATGCACAAATGAGCAGGGCCGGTGGAGTG
                610                          630                           650
GGCGCAGTGCGCTGCCACTGAGGTGTTGCATGATGTTTGGATGCTAGACTAGTTG
                670                          690                           710
CATCTGACGGGAGAAGTTTGTGTTACCAGCCATGCCTTGGAAAGACTTAAGTAATGC
                730                          750                           770
AAAAGGTTGTCCTTTTTTTTTTTTTTAATCTACTGACAAGTTGCTCTAGTAA
                790                          810                           830
CCCAAGAAGTGAAGGAGAAAGCAGCTGCCTCACCGCCCAGACATTGATTGTTCAGATG
                850                          870                           890
TTTCAATGCCTCATGATACAATAAAACCACAAAAATTTCTTAACAAAAAAA
```

FIG. 2 cont.

PROTEIN PP15 PREPARED BY GENETIC MANIPULATION

This application is a continuation of application Ser. No. 324,068, filed Mar. 16, 1989, abandoned.

DESCRIPTION

The protein PP 15, which has an immunosuppressant action, is described in DE-A 29 52 792 (U.S. Pat. No. 4,348,316) with the following parameters:
(a) a carbohydrate content of 3.35±0.9%, composed of 2.8±0.5% hexoses, 0.3±0.2% hexosamines, 0.05±0.05% fucose and 0.20±0.15% neuraminic acid;
(b) sedimentation coefficient $S_{20,w}O$ of 2.9±0.2 S;
(c) a molecular weight determined in the ultracentrifuge of 30,700±3,200 (dimer);
(d) an extinction coefficient $E^{1\%}1$ cm (280 nm) of 14.2±1.0, and
(e) an electrophoretic mobility in the region of that of albumin, as well as
(f) an isoelectric point of 4.4±0.1;
(g) the amino acid composition

| Amino acid | Residues per 100 residues (mol-%) | Coefficient of variation (%) |
|---|---|---|
| Lysine | 4.74 | 3.30 |
| Histidine | 3.81 | 5.43 |
| Arginine | 1.62 | 3.43 |
| Aspartic acid | 13.39 | 5.08 |
| Threonine | 3.85 | 5.35 |
| Serine | 6.38 | 2.81 |
| Glutamic acid | 13.43 | 5.32 |
| Proline | 4.35 | 14.25 |
| Glycine | 6.87 | 2.13 |
| Alanine | 6.51 | 8.26 |
| Cystine ½ | 2.48 | 4.55 |
| Valine | 2.29 | 15.67 |
| Methionine | 2.87 | 10.86 |
| Isoleucine | 8.39 | 8.18 |
| Leucine | 8.18 | 6.72 |
| Tyrosine | 2.09 | 8.49 |
| Phenylalanine | 6.27 | 2.27 |
| Tryptophan | 2.51 | 6.81 |

Determination of the molecular weight by SDS polyacrylamide gel electrophoresis yielded a molecular weight of about 15,000 d (monomer).

Because of the therapeutic interest aroused by the immunosuppressant properties, and of the diagnostic interest, a preparation of this protein by genetic manipulation is extremely desirable. Consequently, the invention relates to a process for the preparation of PP15 by genetic manipulation, to the mRNA necessary for this, to the cDNA obtained therefrom, to DNA structures and vectors containing this DNA in whole or in part, to cells transformed with such DNA, to the polypeptide expressed by these cells, and to the use thereof as pharmaceuticals. The invention further relates to the amino acid sequence and to part-sequences of the amino acid sequence of PP15, to specific antibodies obtained therewith, to diagnostic aids and antibody columns prepared from these antibodies, and to the polypeptide obtained using such columns. A further embodiment of the invention relates to diagnostic aids which contain, in whole or in part, RNA or DNA encoding PP15, or complementary thereto, and to diagnostic methods with which body fluids and tissue are examined using such diagnostic aids. Further aspects of the invention are explained in detail hereinafter and defined in the patent claims.

BRIEF DESCRIPTION OF THE DRAWINGS

FIG. 2 depicts the complete sequence of PP15 cDNA (coding Strand).

Figure 1:
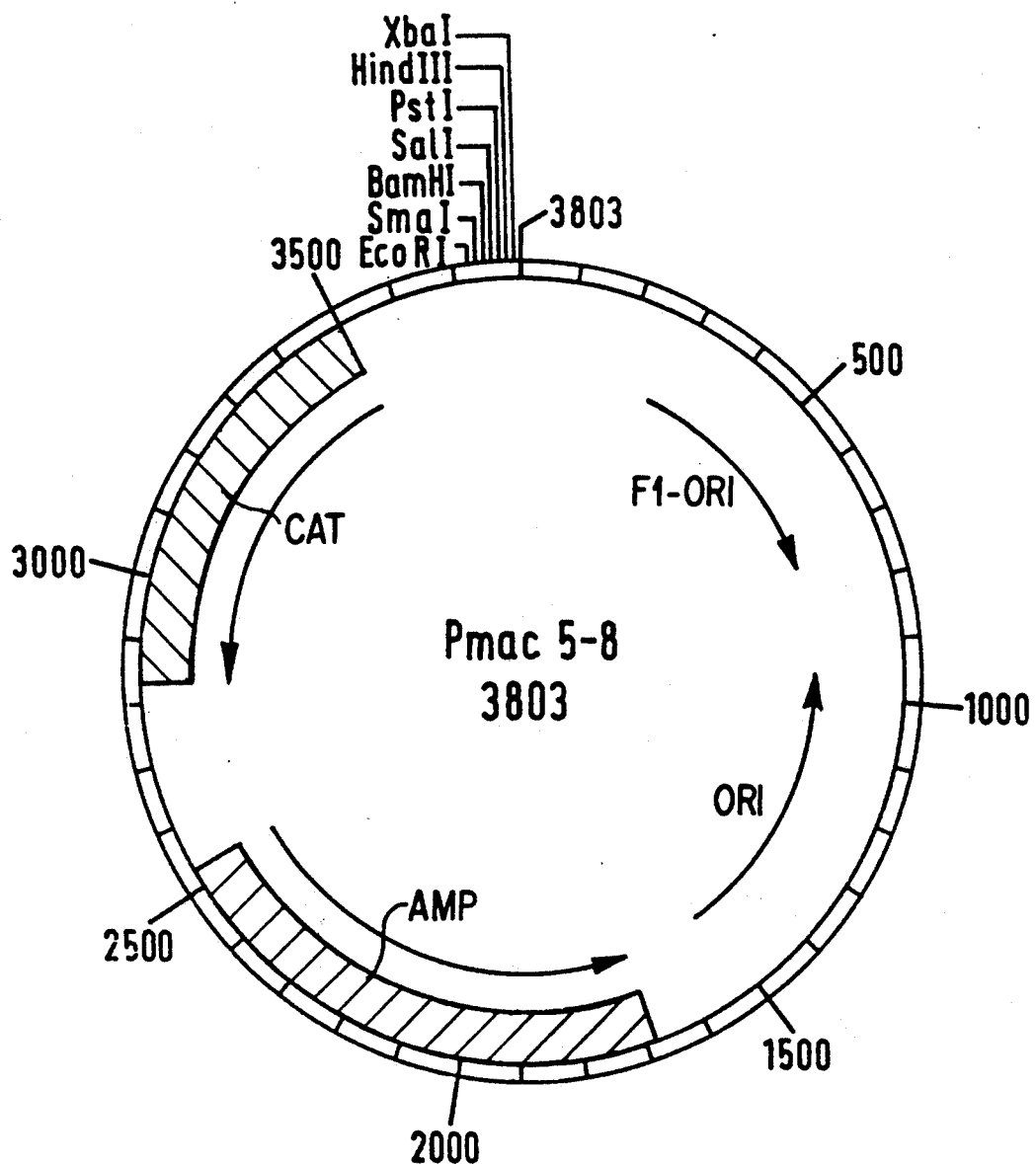
FIG. 1 depicts a map of the plasmid pMac5-8 (=pMa5-8 and pMc5-8). The following abbreviations are used: F1-ORI=origin of replication of the phage f1; ORI=origin of replication of the ColE1 type; CAT=region coding for chloramphenicol acetyltransferase; AMP=region coding for beta-lactamase. pMa5-8 has an amber mutation in CAT (A at position 3409) and pMc5-8 has an amber mutation in AMP (C at position 2238).

Initially, an attempt was made, using specific antibodies against PP15, to detect in a commercially available cDNA expression bank composed of mRNA from mature human placenta (from Genofit, Heidelberg) clones which express PP15. It was known that PP15 has an immunosuppressant action, and consequently it was possible to prepare specific antibodies only unsatisfactorily, if at all, which is why specific antibodies against peptide fragments were prepared.

For this reason, the protein PP15 was broken down by cleavage with cyanogen bromide, trypsin or proteinase V8 into specific fragments which were subsequently sequenced. The following fragments were obtained:
(A) M V V G Q L K A D E D P I M G F H Q M F
(B) F R L A L H N F G
(C) V S V Y A E A A E R
(D) L S S L P F Q K I Q (H)
(E) F D N D R T Q L G A I Y I D A S - L T - E
(F) L L K N I N D A W T Peptides A, B and C were synthesized by generally known methods, and specific antibodies were raised in rabbits by customary processes. It was not possible to locate positive clones in the abovementioned cDNA expression bank, which contained $>1 \times 10^6$ recombinant lambda gt11 clones. Thus, antibodies against peptide A and peptide B precipitated PP15 in control experiments, whereas antibodies against peptide C did not react. Moreover, as will be seen later, peptide C is not present in the protein sequence of PP15 subsequently derived from the cDNA sequence, so that t ought probably to be assigned to concomitant proteins of PP15.

Subsequently, statistical data by R. Lathe (J. Mol. Biol. 1985) 183, 1-12) were used to select from the oligonucleotides coding for PP15 oligopeptide A the PP15 oligonucleotide 103

5'ATGGTGGTGG GCCAGCTGAA GGCTGATGAG GACCCC, and correspondingly from the oligopeptide E the PP15 oligonucleotide 140

5'TTTGACAATG ACCGGACCCA GCTGGGCGCC ATCTACATTG ATGC and from the oligopeptide F a 64-fold degenerate PP15 oligonucleotide 139

```
5'AAAAATATTAATGATGCCTGGAC
      G   C   C   C   C
                      A
```

These oligonucleotide probes were used to screen a cDNA bank prepared from mRNA from mature human placenta. The mRNA was initially isolated from the placenta and then used to prepare the cDNA. The latter was provided with EcoRI ends and ligated into the EcoRI cleavage site of the phage vector lambda gt10. 2 clones (PP15-24 and PP15-28) which contain the complete cDNA of PP15 were detected. DNA sequencing was carried out by methods known per se; the complete sequence of PP15 cDNA (coding strand) is shown in FIG. 2. This cDNA is 894 base-pairs (bp) long, has a 99 bp untranslated sequence at the 5' end, has an open reading frame of 381 bp, and leaves 414 bp, including eight bases of poly(A), untranslated at the 3' end.

The positions of the nucleotide probes are indicated by underlining in FIG. 2, and the amino acid sequence is additionally inserted.

It is possible according to the invention for the coding cDNA to be used, with the aid of suitable expression systems, to express PP15. Furthermore, the type of modification of PP15 can be influenced by the choice of the host. Thus, no glycosylation takes place in bacteria, while that taking place in yeast cells differs from that in higher eukaryotic cells.

Knowing the amino acid sequence of PP15, it is possible to prepare, by conventional or genetic manipulation methods, amino acid part-sequences which can be used as antigens for the preparation of polyclonal or monoclonal antibodies. Such antibodies can be used not only for diagnostic purposes but also for the preparation of antibody columns with which it is possible to separate PP15 from solutions which contain it together with other proteins.

It is also possible using the cDNA, or parts thereof, to isolate in a straightforward manner from a genomic bank the genomic clone which codes for PP15 and which not only facilitates the expression in eukaryotic cells but also allows further diagnostic conclusions to be drawn.

The invention is further defined in the patent claims and is explained in detail in the Examples which follow.

The following abbreviations are used, apart from those explained in the text:
EDTA=sodium ethylenediaminetetraacetate
SDS=sodium dodecyl sulfate
DTT=dithiothreitol
BSA=bovine serum albumin

EXAMPLES

1. Isolation of RNA from human placenta

RNA was obtained from mature human placenta (method of Chirgwin et al., Biochemistry 18 (1979) 5294–5299). About 10 g of placental tissue were ground in liquid nitrogen in a mortar, suspended in 80 ml of 4 M guanidinium thiocyanate containing 0.1 M mercaptoethanol, and treated in a homogenizer (Ultraturrax) at 20,000 rpm for 90 sec. The lysate was centrifuged (Sorvall GSA rotor) at 7,000 rpm for 15 min, and the supernatant was precipitated with 2 ml of 1 M acetic acid and 60 ml of abs. ethanol at $-20°$ C. overnight. The nucleic acids were sedimented at 6,000 rpm and $-10°$ C. for 10 min and then completely dissolved in 40 ml of 7.5 M guanidinium hydrochloride (pH 7.0) and precipitated with a mixture of ml of 1 M acetic acid and 20 ml of abs. ethanol. To remove the DNA, the precipitation was repeated once more with each of the volumes being halved. The RNA was dissolved in 12 ml of $H_2O$, precipitated with a mixture of 1.2 ml of 4 M potassium acetate and 24 ml of abs. ethanol sedimented and, finally, again taken up in 10 ml of $H_2O$ (1 ml per g of tissue).

2. Obtaining poly(A)-containing placental mRNA

To obtain poly(A)-containing mRNA, the placental RNA was fractionated by oligo(dT)-cellulose chromatography (Aviv and Leder, Proc. Natl. Acad. Sci. USA 69 (1973) 1408-1412) in 2 ml Pasteur pipettes in LiCl. About 5 mg of placental RNA in buffer 1 (500 mM LiCl, 20 mM Tris (pH 7.5), 1 mM EDTA, 0.1% SDS) were applied to the column. Whereas the poly(A)+ RNA was bound to oligo(dT)-cellulose, it was possible to elute the poly(A)− RNA again. After a washing step with buffer 2 (100 mM LiCl, 29 mM Tris (PH 7.5), 1 mM EDTA, 0.1% SDS), the poly(A)+ RNA (placental mRNA) was eluted from the column with buffer 3 (5 mM Tris (pH 7.5), 1 mM EDTA, 0.05% SDS).

For further purification, the poly(A)+ RNA hu was adjusted to buffer 1 and again chromatographed on oligo(dT)cellulose. The yield of placental poly(A)+ RNA after this second purification step was about 4% of the RNA used.

3. Synthesis of cDNA from human placenta (placental cDNA) and double-stranded cDNA (dsDNA)

The integrity of the poly(A)-containing placental mRNA was checked in a 1.5% agarose gel before the cDNA synthesis.

Then 4 µg of placental mRNA were dissolved in 65.5 µl of $H_2O$, denatured at 70° C. for 10 min and cooled in ice.

The cDNA was synthesized in a 100 µl mixture after addition of 20 µl of $RT_1$ buffer (250 mM Tris (pH 8.2) at 42° C., 250 mM KCl, 30 mM $MgCl_2$), 2.5 µl of 20 mM dNTP (i.e. all for deoxynucleoside triphosphates), 1 µl of oligo(dT) of 1 µg/ml, 1 µl of 1 M DTT, 2 µl of RNAsin (Boehringer Mannheim) and 8 µl of reverse transcriptase (24 U/µl Boehringer Mannheim) at 42° C. for 90 min. Double-stranded cDNA (dsDNA) was synthesized by the method of Gubler and Hoffmann (Gene 25 (1983) 263–269). The synthesis was carried out immediately after the cDNA synthesis by addition of 305.5 µl of $H_2O$, 80 µl of $RT_2$ buffer (100 mM Tris (pH 7.5), 25 mM $MgCl_2$, 500 mM KCl, 50 mM DTT, 250 µg/ml BSA), 2 µl of RNase H (2 U/µl), 2.5 µl of E. coli DNA ligase (5 U/µl), 5 µl of 15 mM β-NAD, and 5 µl of DNA polymerase I (5 U/µl) and incubation at 15° C. for 5 h. The reaction was stopped by heat inactivation (70° C., 30 min).

After addition of 55 µl of 250 µM dNTP, 55 µl of 10 mM Tris (pH 7.5), 10 mM $MgCl_2$, 10 µg/ml BSA, 3 µl of T4 DNA polymerase I (1 U/µl), 2 µl of RNase H (2 U/µl) and 2 µl of RNase A (2 µg/ml) to the reaction mixture it was incubated at 37° C. for a further 13 min in order to ensure that the synthesis on the second DNA strand was complete ("repair reaction").

4. Ligation of EcoRI linkers to the dsDNA, and opening of the linkers

To set up a placental cDNA bank, the dsDNA was provided with EcoRI ends in order to be able to ligate it into the EcoRI cleavage site of the phage vector λgt10 (T. Maniatis et al. (1982), Molecular Cloning, A Laboratory Manual, Cold Spring Harbor). For this purpose, the dsDNA was a) treated with EcoRI methylase in order to protect internal EcoRI cleavage sites of the dsDNA, and
b) provided with EcoRI linkers which
c) were then opened with EcoRI.

Re a):

The methylase reaction of dsDNA was carried out directly following the repair reaction after addition of 25 µl of 500 mM EDTA (pH 8.0), 60 µl of methylase buffer (100 mM NaOAc (pH 5.2), 2 mg of S-adenosyl-L-methionine) and 2 µl of EcoRI methylase (20 U/µl) by incubation at 37° C. for 30 min.

The reaction mixture was extracted with phenol, and the dsDNA was precipitated with 60 µl of 4 M NaOAc and 1300 µl of ethanol. The dsDNA was washed twice with 70% ethanol, extracted by shaking once with ether, and dried.

Re b):

EcoRI-methylated dsDNA was dissolved in 88 µl of $H_2O$ and, after addition of 10 µl of ligase buffer (500 mM Tris (pH 7.4), 100 mM $MgCl_2$, 100 mM DTT, 100 mM spermidine, 10 mM ATP, 1 mg/ml BSA) and 1 µl of T4 DNA ligase (10 U/µl), was ligated with 1 µl of EcoRI linkers (0.5 µg/µl) (pGG-AATTCC and pA-GAATTCT) at 15° C. overnight.

Re c):

The volume of the ligase mixture was made up to 120 µl with 6 µl of $H_2O$, 12 µl of 10×EcoRI buffer and 2 µl of EcoRI (120 U/µl). The EcoRI digestion was carried out at 37° C. for 2 h.

5. Removal of unbound linkers on a potassium acetate gradient, and selection of the dsDNA for size All unbound EcoRI linkers were removed from the dsDNA by applying the EcoRI reaction mixture in toto to a potassium acetate gradient (5-20% KOAc, 1 mM EDTA, 1 µl/ml ethidium bromide) and centrifuging (Beckman SW 65 rotor) at 50,000 rpm and 20° C. for 3 h.

The gradient was fractionated from below in such a way that the first five fractions measured 500 µl, and all remainders measured 100 µl. The fractions were precipitated with 0.01 volume of acrylamide (2 mg/ml) and 2.5 volumes of ethanol, washed once with 70% strength ethanol and dried, and each was taken up in 5 µl of $H_2O$.

To determine the size of the dsDNA, 1 µl of each fraction was analyzed in a 1.5% agarose gel. In addition, the quantity of dsDNA was determined using 1 µl of each fraction.

Fractions containing dsDNA above 500 bp were combined, and the sample was concentrated until the final concentration was 27 µg/ml.

6. Insertion of the dsDNA into the phage vector λt10, and in vitro packaging reaction The dsDNA was inserted into the EcoRI cleavage site of the phage vector λgt10 (Vector Cloning Systems, San Diego, Calif.) in a 4 µl ligase mixture: 2 µl of dsDNA, 1 µl of λgt10 x EcoRI (1 µg/ml), 0.4 µl of ligase buffer, 0.5 µl of $H_2O$, 0.1 µl of T4 DNA ligase. The mixture was incubated at 15° C. for 4 h.

To establish the placental cDNA bank in the phage vector λgt10, the ligase mixture was subsequently subjected to an in vitro packaging reaction with the λ-lysogenic cell extracts E. coli NS 428 and NS 433 at room temperature for 2 h (Vector Cloning Systems, San Diego, Calif.; Enquist and Sternberg, Methods in Enzymology 68, (1979), 281-298). The reaction was stopped with 500 µl of suspending medium (SM: 0.1 M NaCl, 8 mM $MgSO_4$, 50 mM Tris (pH 7.5), 0.01% gelatin) and 2 drops of chloroform.

7. Titer determination and analysis of the placental cDNA bank

The number of plaque-forming units (PFU) of the placental cDNA bank were determined using competent cells of E. coli K 12 strain C600 HFL: it was $1 \times 10^6$ PFU.

8. Oligonucleotide probes for screening the placental cDNA bank

Oligonucleotide probes (PP15 oligonucleotide 103 and 140) and a pool of oligonucleotides (PP15 oligonucleotide pool 139) were synthesized for the analysis of the placental cDNA bank. Their sequences were derived from the amino acid sequence of three cyanogen bromide fragments of PP15.

The manner of construction and the use of the probes essentially followed the rules of R. Lathe, loc. cit.

The oligonucleotide sequences were labeled at the 5end using T4 polynucleotide kinase in the presence of ($\lambda$-$^{32}$P) ATP (using 60 µCi/40 µl of reaction mixture). The probes had a specific activity of $1 \times 10^8$ Bq/µl or $1.5 \times 10^6$ Bq/pmol.

9. Screening of the placental cDNA with PP15-specific oligonucleotides $1 \times 10^6$ PFU of the placental cDNA bank were examined with the PP15 oligonucleotide probes 103, 140 and 139 together. For this purpose, $3 \times 10^4$ PFU were plated out with cells of the E. coli K 12 strain C 600 HFL in soft agar on 13.5 cm Petri dishes and incubated at 37° C. for 6 h. Lysis was still incomplete at this time. The plates were incubated in a refrigerator overnight, and the phages were transferred to nitrocellulose filters (Schleicher & Schull, BA 85, Ref. No. 401124) (duplicates). The nitrocellulose filters and Petri dishes were marked with an injection needle to allow later assignment of positive plaques. During the processing of the nitrocellulose filters, the Petri dishes were stored in a cold room. The DNA on the nitrocellulose filters was denatured by placing the filters on filter paper (Whatman M3) impregnated with 1.5 M NaCl, 0.5 M NaOH for 5 min. The filters were then renatured in the same way using 1.5 M NaCl, 0.5 M Tris (pH 8.0) and washed with 2×SSPE (0.36 M NaCl, 16 mM NaOH, 20 mM $NaH_2PO_4$, 2 mM EDTA). The filters were then dried in vacuo at 80° C. for 2 h. The filters were washed in 3×SSC, 0.1% SDS (20×SSC=3 M NaCl, 0.3 M Na citrate) at 65° C. for 4 h and prehybridized at 65° C. for 4 h (prehybridization solution: 0.6 M NaCl, 0.06 M Tris (pH 8.3), 6 mM EDTA, 0.2% non-ionic synthetic sucrose polymer (RFicoll), 0.2% polyvinylpyrrolidone 40, 0.2% BSA, 0.1% SDS, 50 µg/ml denatured herring sperm DNA). The filters were incubated overnight with the addition of 100,000-200,000 Bq of the labeled oligonucleotide per ml of hybridization solution (as prehybridization solution but without herring sperm DNA) in beakers or n sealed polyethylene films, shaking gently. The hybridization temperature was 46° C. for oligonucleotide probe 139° and 52° C. for the other two clones PP15-24 and PP15-28 contain the complete cDNA of PP15.

Tab. 1 compares the oligonucleotide sequences 103, 139 and 140 with the PP15 sequence found.

TABLE 1

PP15 sequence vs. PP15 oligonucleotide 103

```
301 ATCACCGCGCAGGACCATCAGCCCACTCCAGATAGCTGCATCATCAGCAT 350
  1 ........................................... AT 2

351 GGTTGTGGGCCAGCTTAAGGCGGATGAAGACCCCATCATGGGGTTCCACC 400
  3 GGTGGTGGGCCAGCTGAAGGCTGATGAGGACCCC............... 36
```

PP15 sequence vs. PP15 oligonucleotide 139

```
401 AGATGTTCCTATTAAAGAACATCAACGATGCTTGGGTTTGCACCAATGAC 450
  1 .............. AAGAACATCAACGATGCCTGGAC............ 23
```

PP15 sequence vs. PP15 oligonucleotide 140

```
151 TACTACCAGTTATTTGATAATGATAGAACCCAACTAGGCGCAATTTACAT 200
  1 ............ TTTGACAATGACCGGACCCAGCTGGGCGCCATCTACAT 38

201 TGACGCGTCATGCCTTACGTGGGAAGGACAACAGTTCCAGGGGAAAGCTG 250
 39 TGATGC..................................... 44
``` probes. The nitro-cellulose filters were washed with 6×SSC, 0.05 M sodium pyrophosphate at room temperature for one hour and at the relevant hybridization temperature for a further hour. The filters were dried and autoradiographed overnight. Signals which appeared on both duplicates of the X-ray film were assigned to the Petri dishes, and the region (about 50 plaques) was punched out with the wide end of a Pasteur pipette, and the phages were resuspended in 1 ml of SM buffer. Positive phages were singled out over three cycles until a single clone was obtained.

Three samples each of 1×10⁶ PFU of the placental cDNA bank were examined. Not until the third screening were 2 signals identified on duplicate filters. The 10. DNA sequence analysis The phage clones PP15-24 and PP15-28 were propagated, and the DNA of each of them was extracted. In each case the EcoRI fragment was isolated and ligated into the EcoRI site of the Bluescript M13 vector (Stratagene, San Diego, Calif., USA) for restriction analyses and sequence analyses using the enzymatic dideoxy method of Sanger. The sequence shows an open reading frame and codes for a protein having a maximum of 127 amino acids. PP15 has a calculated molecular weight of 14478 d (including methionine), which agrees well with the figure, mentioned in the introduction, from the Patent DE-A 2,952,792.

TABLE 2

```
           10                      30                      50
GGAAGGGACAGTCGGCCGCAGACCGCGCTGGGTTGCCGCTGCCGCTGCCGCCATCGTGCC 70                      90                     110
AGCCCCTCGGGTCTCCGTGAGGCCGGGTGACGCTCCAGAATGGGAGACAAGCCAATTTGG
                                            M  G  D  K  P  I  W
          130                     150                    170
GAGCAGATTGGATCCAGCTTCATTCAACATTACTACCAGTTATTTGATAATGATAGAACC
 E  Q  I  G  S  S  F  I  Q  H  Y  Y  Q  L  F  D  N  D  R  T 190                     210                    230
CAACTAGGCGCAATTTACATTGACGCGTCATGCCTTACGTGGGAAGGACAACAGTTCCAG
 Q  L  G  A  I  Y  I  D  A  S  C  L  T  W  E  G  Q  Q  F  Q 250                     270                    290
GGGAAAGCTGCCATTGTGGAGAAGTTGTCTAGCCTTCCGTTCCAGAAAATTCAGCACAGC
 G  K  A  A  I  V  E  K  L  S  S  L  P  F  Q  K  I  Q  H  S 310                     330                    350
ATCACCGCGCAGGACCATCAGCCCACTCCAGATAGCTGCATCATCAGCATGGTTGTGGGC
 I  T  A  Q  D  H  Q  P  T  P  D  S  C  I  I  S  M  V  V  G 370                     390                    410
CAGCTTAAGGCGGATGAAGACCCCATCATGGGGTTCCACCAGATGTTCCTATTAAAGAAC
 Q  L  K  A  D  E  D  P  I  M  G  F  H  Q  M  F  L  L  K  N 430                     450                    470
ATCAACGATGCTTGGGTTTGCACCAATGACATGTTCAGGCTCGCCCTGCACAACTTTGGC
 I  N  D  A  W  V  C  T  N  D  M  F  R  L  A  L  H  N  F  G
```

TABLE 2-continued

```
       490                    510                      530
TGACCTCCTCTCAGCTAGGCACTCACGCTGTTTCCTCCTCCCTCCTCTTCCCAATACTAT 550                    570                      590
TCCCACTCCTCCAGATGCTCCAAATATCATGCACAAATGAGCAGGGCCGCGGTGGGAGTG 610                    630                      650
GGCGCAGTGCGCTGCTGCCACTGAGGTGTTGTGCATGATGTTTGGATGCTAGACTAGTTG 670                    690                      710
CATCTGACGGGAGAAGTTTGTGTTGTACCAGCGCATGCCTTGGAAAGACTTAAGTAATGC 730                    750                      770
AAAAGGTTGTCCTTTTTTTTTTTTTTTTTTTTTTTAATCTACTGACAAGTTGCTCTAGTAA 790                    810                      830
CCCAAAGAAGTGAAGGAGAAAGCAGCTGCCTCACCGCCCAGACATTGATTTGTTCAGATG 850                    870                      980
TTTCAATGCCTCATGATACAATAAAACCACAAAAATTTTCTTAACAAAAAAAAA
```

11. Expression of the immunosuppressive protein PP15

The vector pTrc99A (E. Amann et al. (1988) Gene 69, 301-15) was used to express the non-fused mature PP15 protein in E. coli. The DNA sequence of the PP15 cDNA at the ini-tiation codon is as follows:

```
                     Met Gly Asp
5' ... CGCTCCAGA ATG GGA GAC ... 3'
```

Since there is no NcoI site at the ATG, it is impossible for this DNA to be cloned directly into the pTrc99A expression vector. However, an NcoI site can be achieved by mutagenesis, by two base-exchanges in the PP15 sequence: 5' GAATGG 3' to 5' CCATGG 3'. The second amino acid (Gly) is unaffected by this manipulation, because the second codon of the PP15 structural sequence starts with a "G". For the mutagenesis, an EcoRI fragment 902 base-pairs in size was isolated from the PP15 cDNA clone PP15-28 and ligated into the mutagenesis vector pMa5-8 (FIG. 1) which had likewise been cut with EcoRI and had been dephosphorylated. The resulting plasmid pMa5-8-PP15 (with the correct orientation of the PP15 EcoRI insert in relation to F1-oriλ was then subjected to the gapped duplex mutagenesis protocol (Kramer et al. (1984) Nucl. Acids. Res. 12, 9441-9456), using the following oligodeoxynucleotide:

5' GGCTTGTCTCCCATGGTGGAGCGTCAC 3'

One clone which had the desired mutation was identified by restriction analysis and was called pMc5-8-PP15-NcoI. The NcoI-EcoRI fragment 798 base-pairs in size was isolated from this plasmid and ligated into the correspondingly cut pTrc99A vector. The resulting plasmid pTrc-99A-PP PP15 embraces 4918 base-pairs and, after induction of the trc promoter, expresses the non-fused PP15 protein about 15 kD in size.

We claim:

1. An isolated DNA sequence coding for protein PP15 having immunosuppressant activity and the amino acid sequence shown in FIG. 2.

2. An isolated DNA sequence containing the coding strand shown in FIG. 2.

3. Recombinant plasmid or vector containing said DNA sequence of claim 1.

4. Recombinant plasmid or vector containing said DNA sequence of claim 2.

5. A transformed cell containing DNA as claimed in claim 1.

6. A transformed cell containing DNA as claimed in claim 3.

7. A transformed cell containing said recombinant plasmid or vector as claimed in claim 3.

8. A process for the preparation of PP15, which comprises insertion of a DNA sequence as claimed in claim 1 into an expression system, and bringing about expression therein.

9. A process for the preparation of PP15, which comprises insertion of a DNA sequence as claimed in claim 2 into an expression system, and bringing about expression therein.

10. A method of detecting in a biological sample DNA sequences complementary to the isolated DNA sequence of claim 1, comprising:
 (a) transferring DNA from said biological sample to a hybridizable filter;
 9b) denaturing the DNA on said filter;
 (c) hybridizing the DNA on said filter to a DNA probe comprising said isolated DNA sequence of claim 1; and
 (d) detecting possible hybrids between said probe and said DNA from a biological sample.

11. A process for the preparation of PP15, as claimed in claim 14, wherein the expression system comprises E. coli.

12. A process for the preparation of PP15, as claimed in claim 14, wherein the expression system comprises yeast.

* * * * *

UNITED STATES PATENT AND TRADEMARK OFFICE
CERTIFICATE OF CORRECTION

PATENT NO. : 5,188,933
DATED : February 23, 1993
INVENTOR(S) : Ulrich Grundmann et al It is certified that error appears in the above-indentified patent and that said Letters Patent is hereby corrected as shown below:

Claim 6, column 10, line 33, change "claim 3"
to --claim 2--.

Claim 10, column 10, line 48, change "9b)"
to --(b)--.

Claim 11, column 10, line 56, change "claim 14"
to --claim 8--.

Claim 12, column 10, line 59, change "claim 14"
to --claim 8--.

Signed and Sealed this

Twenty-fifth Day of January, 1994

Attest:

BRUCE LEHMAN

Attesting Officer

Commissioner of Patents and Trademarks